(12) United States Patent
Sami et al.

(10) Patent No.: US 8,229,540 B2
(45) Date of Patent: Jul. 24, 2012

(54) METHOD FOR SEPARATING MULTICHANNEL SIGNALS PRODUCED BY AC AND DC SOURCES FROM ONE ANOTHER

(75) Inventors: Taulu Sami, Helsinki (FI); Kajola Matti, Helsinki (FI); Simola Juha, Helsinki (FI)

(73) Assignee: Elekta AB (SE)

( * ) Notice: Subject to any disclaimer, the term of this patent is extended or adjusted under 35 U.S.C. 154(b) by 1101 days.

(21) Appl. No.: 10/586,448

(22) PCT Filed: Jan. 19, 2005

(86) PCT No.: PCT/FI2005/000038
§ 371 (c)(1),
(2), (4) Date: Nov. 24, 2008

(87) PCT Pub. No.: WO2005/067789
PCT Pub. Date: Jul. 28, 2005

(65) Prior Publication Data
US 2009/0069661 A1 Mar. 12, 2009

(30) Foreign Application Priority Data
Jan. 19, 2004 (FI) ..................................... 20040070

(51) Int. Cl.
*A61B 5/05* (2006.01)
(52) U.S. Cl. ........ 600/407; 600/409; 324/244; 324/248; 324/301; 324/302
(58) Field of Classification Search .......... 600/407–409; 324/244–263, 301, 302; 702/66
See application file for complete search history.

(56) References Cited

U.S. PATENT DOCUMENTS

| | | | |
|---|---|---|---|
| 4,793,355 A | 12/1988 | Crum et al. | |
| 5,408,178 A | 4/1995 | Wikswo, Jr. et al. | |
| 5,494,035 A | 2/1996 | Leuthold et al. | |
| 7,062,391 B2 * | 6/2006 | Wilson ........................... | 702/64 |
| 2002/0151779 A1 | 10/2002 | Avrin et al. | |

FOREIGN PATENT DOCUMENTS

| | | |
|---|---|---|
| EP | 0 483 698 B1 | 4/1995 |
| JP | 4-135536 | 5/1992 |

OTHER PUBLICATIONS

Samu Taulu, et al., International Congress Series 1270 (2004), 32-37, Aug. 2004, Clinical applications of the signal space separation method.
International Search Report for PCT/FI2005/000038 dated May 27, 2005.

* cited by examiner

*Primary Examiner* — Brian Casler
*Assistant Examiner* — Daniel Huntley
(74) *Attorney, Agent, or Firm* — Studebaker & Brackett PC; Donald R. Studebaker

(57) ABSTRACT

The present invention relates to a novel manner of measuring DC fields using a multi-channel MEG or MKG measuring instrument; and on the other hand, to a manner of eliminating from the measurement result the interference signals caused by the DC currents. The invention combines the monitoring system of a testee's movement and the method for motion correction of the measured signals so that the signals produced by the DC currents of a moving testee's are visible in the final measurement result as a static signal component in a conventional MEG or MKG measurement. In that case, in the measurement, it is not necessary to beforehand prepare oneself for measuring the DC fields.

10 Claims, 1 Drawing Sheet

Figure 1:
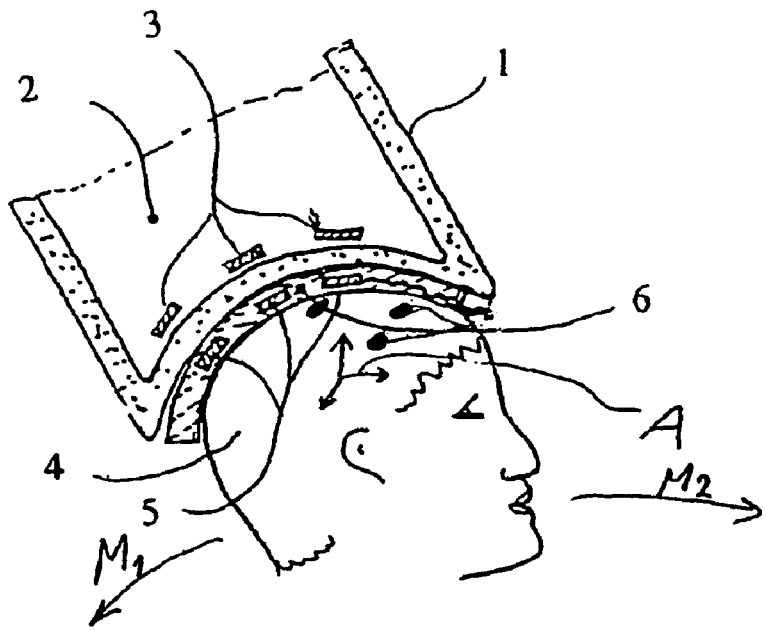

METHOD FOR SEPARATING MULTICHANNEL SIGNALS PRODUCED BY AC AND DC SOURCES FROM ONE ANOTHER

FIELD OF THE INVENTION

The present invention relates to a novel and advanced method for processing magnetic fields, so-called DC fields, produced by currents independent of time, i.e. DC currents, in multichannel measurements. In particular, the invention relates to a novel manner of eliminating the harmful DC fields caused by the motion of an object being monitored, and on the other hand to a manner of studying interesting DC fields.

In conjunction with this invention, static DC sources, fields and currents independent of time are used to mean both completely static phenomena and those varying at the frequency of one Hertz at the most.

BACKGROUND OF THE INVENTION

For measuring biomagnetic signals, magnetometers such as SQUID sensors are usually used, which are sensitive just to dynamic phenomena. In this manner, the DC currents of an object that is immovable with respect to a set of sensors do not cause a measurement signal; and the only way to measure the DC currents is to move the object with respect to the set of sensors. In that case, a static magnetic field distribution produced by the DC currents in the co-ordinates of the object changes in the co-ordinates of the set of sensors as a function of time, thus causing a measurement signal that changes as a function of time.

The DC currents producing DC fields are not usually very interesting, but e.g. in the magnetoencephalographic i.e. MEG measurements there are situations in which it is desirable to perceive DC currents. Interesting DC currents are associated e.g. with epilepsy, migraine and REM phases of sleep.

In addition to the DC fields caused by physiological DC currents, DC fields are produced by all the immovable magnetised articles in the co-ordinates of an object. These can include tiny magnetic particles left in the skull by a drill used in a brain surgery, as well as magnetic impurities e.g. in the hair. As the object moves, magnetisations of this kind typically produce a very strong interference signal compared to a biomagnetic signal, the elimination and attenuation of which is necessary in order to perceive the physiological phenomenon being studied.

The problem is a typical one specifically in clinical measurements which measure patients who find it difficult to stay completely immovable during the measurement. In addition to the MEG measurements, the DC fields produced by DC currents can be of importance e.g. in the magnetocardiogpraphic i.e. MKG measurements to be made to study cardiac functions, in which magnetised particles produce a measurement signal e.g. as a result of respiratory movements.

To perceive physiological DC currents, a method has been used in which a testee is moved with respect to his or her geometry in a manner known se, e.g. periodically at a known frequency and amplitude with respect to the measuring instrument. One such method has been described e.g. in the publications "*Measurement of near-DC biomagnetic fields of the head using a horizontal modulation of the body position*", Wuebbeler et al, Recent Advances in Biomagnetism, Sendai, pp. 369-372, 1999 and "*Hyperventilation-induced human cerebral magnetic fields non-invasively monitored by multi-channel 'direct current' magnetoencephalography*", Carbon et al, Neuroscience Letters, Vol. 287, pp. 227-230, 2000. In the method in question, the testee is lying on a bed that is movable with respect to the set of sensors so that the testee's head is supported to be immovable with respect to the bed. This must be done in order that the movement of the head can be assumed to correspond to a known movement of the bed. The bed is moved sinusoidally at the frequency of 0.4 Hz and at the amplitude of 75 mm, whereby the DC currents of the head are visible in the measurement signal at the modulation frequency of 0.4 Hz. The signals are demodulated and reconstructed in a manner enabling one- to easily study the DC signals.

The method described above relates to the measurement of interesting physiological DC currents using a magnetoencephalographic apparatus. In the method, the head's own movement is prevented and a movement that is necessary for perceiving DC signals is produced using a means, i.e. a bed. In that case, the magnetisation of the bed also produces a signal of the modulation frequency, which as being an interference signal, must be eliminated e.g. by moving the bed in a corresponding manner without the testee, and by measuring the DC signal due to this so as to be the reference.

Several problems and limitations are associated with the method described above. Especially patients in poor health may experience fastening their head unpleasant. Furthermore, the movement of the bed produces the aforementioned interference signal, the elimination of which, as well as the building of a mechanical movement system and the preparation of DC measurements require a lot of additional work compared to a conventional MEG measurement. Thus, the method is very susceptible to interference.

To eliminate the interference signals produced by "additional" DC fields of a movable testee that are associated with conventional MEG measurements, one has not presented any manner based on the DC property of interference sources. The methods of interference elimination do not take into account the movement of the testee; instead they just try to eliminate the interference signal caused by movement from the measurements using standard methods. This can be implemented e.g. using high-pass filtering, but the slow brain signals are lost at the same time.

OBJECTIVE OF THE INVENTION

The objective of the present invention is to eliminate the disadvantages referred to above or at least to significantly alleviate them. One specific objective of the present invention is to disclose a new type of method which, on the one hand, can be used to examine the interesting physiological DC fields of the testee, and on the other hand, to eliminate the distortions caused by "additional" DC fields in a conventional MEG or MKG measurement. Further, the objective of the present invention is to disclose a solution which can be used examine interesting DC fields without specific test arrangements and which enables free movement of the testee's head.

As for the features characteristic of the invention, reference is made to them in the claims.

DESCRIPTION OF THE INVENTION

The present invention relates to a novel manner of measuring DC fields using a multichannel MEG or MKG measuring instrument, and on the other hand, to a manner of eliminating from the measurement result the interference signals produced by DC currents. The invention combines the monitoring system of the movement of a testee and the method for motion correction of the measured signals so that the signals produced by the DC currents of a moving testee are visible "in" the final measurement result as a static signal component in a conventional MEG or MKG measurement. In that case, in the measurement, there is no need for specifically preparing oneself for the measurement of the DC fields in advance. The aforementioned monitoring system of movement has been described in patent application PCT/FI02/00225 and the method for motion correction in patent application FI20030392. They are incorporated herein by a reference.

The basic idea of the invention is that the movement of a testee's head is monitored, and the movement of the head is modelled as the movement of a set of sensors around an immovable head. The measured magnetic field signal is presented as elementary fields in a signal space basis whose basis vector coefficients have been attached to the co-ordinates of the head utilising the information on the geometry between the head and the measuring instrument. In that case, the behaviour over time of the basis vector coefficients does not involve the distortion caused by the movement of the head; instead the same basis vector coefficients would have also been obtained with a completely immovable head, though with that distinction that in the immovable cases, the coefficients would not have a DC component because SQUID sensors do no measure static phenomena. As the head moves with respect to the measuring instrument, a signal produced by the DC currents appears in the measurement signal, the behaviour over time of which in a non-motion corrected measurement corresponds to the movement of the head. As a result of the aforementioned motion monitoring and motion correction method, the perceived signal produced by a DC current appears in the basis vector coefficients as a static signal because in the co-ordinates of the head, the DC currents produce a static signal.

In calculating the elementary fields, an advantageous embodiment is the use of spherical harmonic functions, enabling one to easily eliminate the portion of external interference fields at the same time, as presented in patent application FI20030392. The motion correction can also be made in other manners, e.g. utilising the minimum norm estimate of the current distribution of an object being examined.

Thanks to the invention, the processing of signals produced by DC currents is very easy. To examine physiological DC currents, the testee can be requested to freely move his or her head, whereby as a result of motion correction, the DC component of a measurement signal only contains the signal produced in the testee's head by continuous DC currents. A DC component can be separated e.g. by means of a Fourier conversion.

A. DC signal obtained by a manner described above naturally is the sum of signals produced by all the DC currents, and contains in addition to the physiological DC signals, also the DC signals of the possible magnetic impurities that can be classified as interference sources, which must be separated from the physiological signals by some method. The elimination of a DC interference from motion corrected data is very easy when the physiological DC signal is not the subject of the examination, because a DC signal can be simply eliminated using a so-called baseline correction. In this correction method, the mean value of a signal is calculated in each measurement channel over a time during which there is no biomagnetic response. In that case, the mean value corresponds to the DC level of the channel, which can be eliminated along the entire measurement period by deducting the numerical value of the DC level in question from the measurement signal.

The invention also enables a novel manner for locating an object being measured with respect to the measuring instrument. As the magnetised articles produce a signal, corresponding to the movement of the object, it is possible to attach to the object, to known places, in the co-ordinates of the object, magnetic articles, and to measure the movement of the object based on the motion signals of the articles. In that case, the motion monitoring system corresponds to the method described in patent application FI20010558 with the distinction that static signal transmitters are used herein, and the positioning can be performed, if desired, directly from the spatial distribution of the motion signals without the time integration, enabling one to achieve a considerably faster motion monitoring system, a real-time one in practise.

The present invention enables one to examine the physiological, interesting DC fields of a testee on the one hand; and on the other hand, to eliminate the distortions caused in the measurement signal by "additional" DC fields in a conventional MEG or MKG measurement. Thanks to the invention, specific arrangements are unnecessary in these examinations; instead the solution of the invention, when combined with the conventional measurements, gives a possibility to examine DC currents. Further, the invention enables free movement of the testee's head when measuring DC fields.

LIST OF FIGURES

Figure 2:
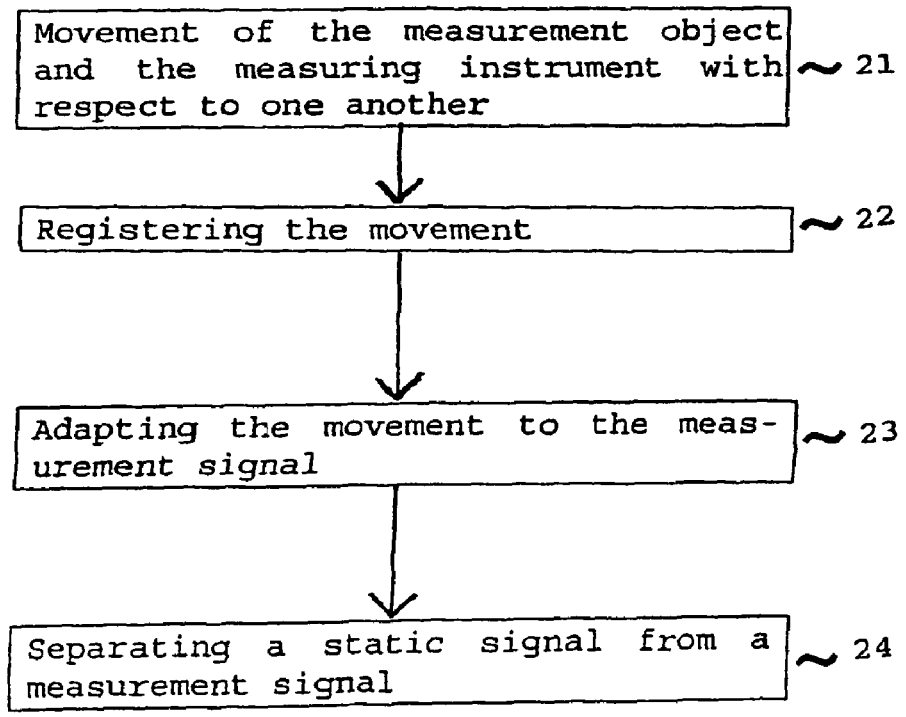

In the following section, the invention will be described in more detail with reference to the accompanying drawings, in which FIG. 1 schematically represents one measurement arrangement in accordance with the present invention; and FIG. 2 is a flow chart illustrating one embodiment in accordance with the present invention.

DETAILED DESCRIPTION OF THE INVENTION

FIG. 1 is one advantageous measurement arrangement according to the invention. FIG. 1 illustratively and schematically represents a multi-channel magnetometer 1, which is designated for the measurement of the magnetic fields of the brain. The magnetometer includes a cooled vessel such as a Dewar vessel 2, having inside thereof at a low temperature a set of individual magnetometers i.e. SQUID sensors 3. Arranged in the object being examined 4, herein on the surface of a testee's head, are a set of signal sources 5, whose location in co-ordinates. A of the measurement object is known. As the location of the signal sources is known, it is possible, by measuring using the set of sensors 3, to find out the location of the signal sources and also the location of the other signal sources in the measurement object, specifically that of the interesting biomagnetic signal sources.

As the measurement object 4 moves, e.g. as shown by arrows $M_1$ and $M_2$, also the signal sources 5 move, whereby the sensors 3 also register the magnetic fields due to the direct current. Thus, the signal sources can be both direct current and alternating current sources.

In the following section, the functioning of the invention is explained with reference to FIGS. 1 and 2. The patent can be requested to move his or her head with respect to the measuring instrument 2, e.g. in the direction of arrows $M_1$ and $M_2$, step 22. The movement can be free, and there is no need to determine it beforehand. The movement is registered using the set of sensors 3, step 23, by utilising the signal sources 5 arranged in the patient's head. The dc sources 6 in the patient's head, which can be associated with interesting biomagnetic phenomena or magnetic pieces, produce a direct current component in the magnetic field in the co-ordinates of the head, which is registered by the sensors 3 due to the dynamics caused by the movement of the head. This detected direct current component can be separated from the measurement signal provided that it is presented by means of the elementary field components attached to the co-ordinates of the head taking into account the detected movement, whereby the dc component is visible as a static signal, steps 23, 24 in FIG. 2. The elementary fields can be generated e.g. in the co-ordinates of the head by means of the spherical harmonic functions presented.

The invention is not limited merely to the embodiment examples referred to above; instead many variations are possible within the scope of the inventive idea defined by the claims.

The invention claimed is:

1. A method of signal processing which is used to separate from a signal registered using a measuring instrument that measures a dynamic phenomenon, a signal associated with a static source in a measurement object, in which method the measurement object and the measuring instrument move with respect to one another, wherein the measurement object is freely movable, the method further comprising: measuring magnetic fields of the measurement object with a multichannel magnetometer; determining the movement
- of the measuring instrument and the measurement object with respect to one another based on the signal registered using the measuring instrument;
- modelling the movement of the measurement object as a movement of the measuring instrument around the measurement object;
- presenting the signal registered as elementary fields in a signal space basis whose basis vector coefficients have been attached to the co-ordinates of the measurement object based on a known geometry between the measurement object and the measuring instrument, whereby the signal produced by a static source is detected as a static signal; and
- separating the aforementioned static signal from the signal registered; wherein the measurement object is a brain.

2. The method as defined in claim 1, characterised in that the movement of the measuring instrument and the measurement object is determined in real time when registering a signal.

3. The method as defined in claim 2, characterised in that at least a portion of external interference fields is eliminated within the presentation of the elementary fields.

4. The method as defined in claim 3, characterised in that the elementary fields are calculated using spherical harmonic functions.

5. The method as defined in claim 1, characterised in that the determined movement is corrected by using the minimum norm estimate of the current distribution of the measurement object.

6. The method as defined in claim 1, characterised in that the static signal is separated from the measurement signal by a high-pass filter.

7. The method as defined in claim 1, characterised in that
- dividing the signal registered into two periods of time;
- separating the aforementioned static signal over either one of the periods of time;
- calculating the difference between the signal registered and the separated static signal over the entire period of time.

8. The method as defined in claim 1, characterised in that the movement of the measuring instrument and the measurement object with respect to one another is achieved so that a person being monitored moves his or her intentionally.

9. The method as defined in claim 1, characterised in that
- measuring the signal caused by magnetic pieces attached to the measurement object, whose location in the co-ordinates of the measurement object is known; and
- determining the location of the measurement object in relation to the measuring instrument using the signal registered.

10. The method as defined in claim 1 for reducing an interference caused by the movement of a static magnetisation in a biomagnetic signal, characterised in that the signal registered is high-pass filtered both prior to presenting the signal registered in the co-ordinates attached to the measurement object and after the presentation.

* * * * *

UNITED STATES PATENT AND TRADEMARK OFFICE
CERTIFICATE OF CORRECTION

PATENT NO.         : 8,229,540 B2
APPLICATION NO.    : 10/586448
DATED              : July 24, 2012
INVENTOR(S)        : SamuTaulu, Matti Kajola and Juha Simola It is certified that error appears in the above-identified patent and that said Letters Patent is hereby corrected as shown below:

Title Page, Item (12) United States Patent, should read
    Taulu et al.

Title Page, Item (75) Inventors should read: Samu TAULU, Matti KAJOLA, Juha SIMOLA Signed and Sealed this
Eighteenth Day of December, 2012

David J. Kappos
*Director of the United States Patent and Trademark Office*